(12) United States Patent
D'Souza et al.

(10) Patent No.: US 8,802,603 B2
(45) Date of Patent: Aug. 12, 2014

(54) MEDICAL COMPONENTS HAVING COATED SURFACES EXHIBITING LOW FRICTION AND LOW REACTIVITY

(75) Inventors: Ajit Joseph M. D'Souza, Cary, NC (US); David B. Montgomery, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 307 days.

(21) Appl. No.: 13/161,618

(22) Filed: Jun. 16, 2011

(65) Prior Publication Data

US 2011/0313363 A1    Dec. 22, 2011

Related U.S. Application Data

(60) Provisional application No. 61/355,651, filed on Jun. 17, 2010.

(51) Int. Cl.
*A61L 31/14* (2006.01)
*B05D 5/08* (2006.01)
*C23C 16/00* (2006.01)

(52) U.S. Cl.
USPC ............ 508/173; 508/200; 604/265; 442/569

(58) Field of Classification Search
USPC ....................................................... 508/200
See application file for complete search history.

(56) References Cited

U.S. PATENT DOCUMENTS

| | | |
|---|---|---|
| 4,181,223 A | 1/1980 | Millet |
| 4,452,679 A | 6/1984 | Dunn et al. |
| 4,496,695 A | 1/1985 | Sugio et al. |
| 4,500,310 A | 2/1985 | Christinger |
| 4,720,521 A | 1/1988 | Spielvogel et al. |
| 4,764,576 A | 8/1988 | Ogawa et al. |
| 4,767,414 A | 8/1988 | Williams et al. |
| 4,806,430 A | 2/1989 | Spielvogel et al. |
| 4,822,632 A | 4/1989 | Williams et al. |
| 4,842,889 A | 6/1989 | Hu et al. |
| 4,844,986 A | 7/1989 | Karakelle et al. |
| 4,959,402 A | 9/1990 | Williams et al. |
| 4,994,552 A | 2/1991 | Williams et al. |

(Continued)

FOREIGN PATENT DOCUMENTS

| | | |
|---|---|---|
| CA | 2238213 | 11/1998 |
| DE | 19700079 A1 | 1/1998 |

(Continued)

OTHER PUBLICATIONS

Freeman, "Silicones an Introduction to Their Chemistry and Applications," 1962, 4 pages, The Plastics Institute, ILIFE Books, Ltd., London.

(Continued)

*Primary Examiner* — Jim Goloboy
(74) *Attorney, Agent, or Firm* — The Webb Law Firm (57) ABSTRACT

This invention relates to medical articles, such as a syringe assemblies, including a substrate having a coating on a surface thereof, the coating including: (1) at least one organopolysiloxane and (2) a deposition product applied to the at least one organopolysiloxane by plasma-enhanced chemical vapor deposition of a composition including at least one monomer selected from the group consisting of N-vinyl pyrrolidone, vinyl acetate, ethylene oxide, alkyl acrylate, alkyl methacrylate, acrylamide, acrylic acid, and mixtures thereof, and methods of making and using the same.

26 Claims, 6 Drawing Sheets

(56) References Cited

U.S. PATENT DOCUMENTS

| | | |
|---|---|---|
| 4,997,423 A | 3/1991 | Okuda et al. |
| 5,034,482 A | 7/1991 | Kohara et al. |
| 5,186,972 A | 2/1993 | Williams et al. |
| 5,266,359 A | 11/1993 | Spielvogel |
| 5,288,560 A | 2/1994 | Sudo et al. |
| 5,320,875 A | 6/1994 | Hu et al. |
| 5,338,312 A | 8/1994 | Montgomery |
| 5,536,582 A | 7/1996 | Prasad et al. |
| 5,578,340 A | 11/1996 | Ogawa et al. |
| 5,587,244 A | 12/1996 | Flinchbaugh |
| 5,599,882 A | 2/1997 | Nishi et al. |
| 5,604,038 A | 2/1997 | Denes et al. |
| 5,607,400 A | 3/1997 | Thibault et al. |
| 5,610,253 A | 3/1997 | Hatke et al. |
| 5,623,039 A | 4/1997 | Hatke et al. |
| 5,650,471 A | 7/1997 | Abe et al. |
| 5,736,251 A | 4/1998 | Pinchuk |
| 5,766,362 A | 6/1998 | Montgomery |
| 5,798,220 A | 8/1998 | Kossovsky |
| 5,849,369 A | 12/1998 | Ogawa |
| 5,853,894 A | 12/1998 | Brown |
| 5,854,349 A | 12/1998 | Abe et al. |
| 5,856,414 A | 1/1999 | Hatke et al. |
| 5,866,662 A | 2/1999 | Hatke et al. |
| 5,885,566 A * | 3/1999 | Goldberg .................. 424/78.18 |
| 5,888,591 A | 3/1999 | Gleason et al. |
| 6,046,143 A | 4/2000 | Khan et al. |
| 6,063,886 A | 5/2000 | Yamaguchi et al. |
| 6,065,270 A | 5/2000 | Reinhard et al. |
| 6,153,269 A | 11/2000 | Gleason et al. |
| 6,156,435 A | 12/2000 | Gleason et al. |
| 6,156,566 A | 12/2000 | Bryant |
| 6,200,627 B1 | 3/2001 | Lubrecht |
| 6,243,938 B1 | 6/2001 | Lubrecht |
| 6,293,222 B1 | 9/2001 | Paquet |
| 6,296,893 B2 | 10/2001 | Heinz et al. |
| 6,335,029 B1 | 1/2002 | Kamath et al. |
| 6,383,642 B1 | 5/2002 | Le Bellac et al. |
| 6,443,942 B2 | 9/2002 | Van Antwerp et al. |
| 6,447,835 B1 | 9/2002 | Wang et al. |
| 6,458,867 B1 | 10/2002 | Wang et al. |
| 6,461,334 B1 | 10/2002 | Buch-Rasmussen et al. |
| 6,482,509 B2 | 11/2002 | Buch-Rasmussen et al. |
| 6,486,264 B1 | 11/2002 | Tsunogae et al. |
| 6,506,457 B2 | 1/2003 | Hum |
| 6,511,756 B1 | 1/2003 | Obuchi et al. |
| 6,525,144 B1 | 2/2003 | Tanahashi et al. |
| 6,562,010 B1 | 5/2003 | Gyure et al. |
| 6,586,039 B2 | 7/2003 | Heinz et al. |
| 6,653,424 B1 | 11/2003 | Sakamoto et al. |
| 6,746,430 B2 | 6/2004 | Lubrecht |
| 6,866,656 B2 | 3/2005 | Tingey et al. |
| 6,908,970 B2 | 6/2005 | Tsunogae et al. |
| 6,951,898 B2 | 10/2005 | Hammond et al. |
| 6,995,226 B2 | 2/2006 | Taguchi et al. |
| 7,026,401 B1 | 4/2006 | Osan et al. |
| 7,037,993 B2 | 5/2006 | Taguchi et al. |
| 7,041,088 B2 | 5/2006 | Nawrocki et al. |
| 7,404,278 B2 | 7/2008 | Wittland et al. |
| 7,540,382 B2 | 6/2009 | Samaritani et al. |
| 7,553,529 B2 | 6/2009 | Sakhrani et al. |
| 7,943,242 B2 | 5/2011 | Liu et al. |
| 2001/0004466 A1 | 6/2001 | Heinz et al. |
| 2003/0100696 A1 | 5/2003 | Muraki |
| 2004/0082917 A1 | 4/2004 | Hetzler et al. |
| 2004/0209784 A1 | 10/2004 | Hardman et al. |
| 2006/0105099 A1 | 5/2006 | Takahashi et al. |
| 2006/0251693 A1 | 11/2006 | Short et al. |
| 2006/0252046 A1 | 11/2006 | Short et al. |
| 2007/0148326 A1 | 6/2007 | Hastings et al. |
| 2007/0187280 A1 | 8/2007 | Haines et al. |
| 2007/0228669 A1 | 10/2007 | Liu et al. |
| 2007/0235890 A1 | 10/2007 | Pryce et al. |
| 2007/0253984 A1 | 11/2007 | Khandke et al. |
| 2007/0287954 A1 | 12/2007 | Zhao et al. |
| 2007/0289492 A1 | 12/2007 | Wynne et al. |
| 2008/0069970 A1 * | 3/2008 | Wu .............................. 427/553 |
| 2008/0071228 A1 | 3/2008 | Wu et al. |
| 2009/0117268 A1 | 5/2009 | Lewis et al. |
| 2009/0126404 A1 | 5/2009 | Sakhrani et al. |
| 2009/0155490 A1 | 6/2009 | Bicker et al. |

FOREIGN PATENT DOCUMENTS

| | | |
|---|---|---|
| EP | 0164583 A2 | 12/1985 |
| EP | 0787823 A2 | 8/1997 |
| EP | 879607 A2 * | 11/1998 |
| EP | 0879607 A2 | 11/1998 |
| EP | 1227126 A1 | 7/2002 |
| EP | 1064037 B1 | 7/2004 |
| EP | 1745807 A2 | 1/2007 |
| EP | 0920542 B1 | 10/2007 |
| EP | 2251452 A2 | 11/2010 |
| JP | 57182418 A | 11/1982 |
| JP | 5339505 A | 12/1993 |
| JP | 200597401 A | 4/2005 |
| WO | 9944754 A1 | 9/1999 |
| WO | 9944755 A1 | 9/1999 |
| WO | 9947192 A1 | 9/1999 |
| WO | 2004009146 A1 | 1/2004 |
| WO | 2004064901 A2 | 8/2004 |
| WO | 2004083348 A2 | 9/2004 |
| WO | 2004100862 A2 | 11/2004 |
| WO | 2007081814 A2 | 7/2007 |
| WO | 2007115156 A2 | 10/2007 |
| WO | 2007115159 A2 | 10/2007 |
| WO | 2007120507 A2 | 10/2007 |
| WO | 2008034058 A2 | 3/2008 |
| WO | 2008034060 A2 | 3/2008 |
| WO | 2008112071 A1 | 9/2008 |
| WO | 2009003010 A2 | 12/2008 |
| WO | 2009053947 A2 | 4/2009 |
| WO | 2010034004 A1 | 3/2010 |
| WO | 2010047825 A1 | 4/2010 |

OTHER PUBLICATIONS

Abstract Polycyclic Olefins, Process Economics Report 223, Jul. 1998, 9 pages.

Material Safety Data Sheet for LSR Topcoat Part A, GE Silicones, Jan. 20, 2004, pp. 1-7.

Material Safety Data Sheet for LSR Topcoat Part B, GE Silicones, Jan. 22, 2004, pp. 1-8.

* cited by examiner

UNIFORM COATING ON TIP AND FLANGE

FIG. 3

IRREGULAR COATING IN MIDDLE

MEDICAL COMPONENTS HAVING COATED SURFACES EXHIBITING LOW FRICTION AND LOW REACTIVITY

BACKGROUND OF THE INVENTION

1. Field of the Invention

This invention relates to medical components, such as a syringes, tubes or medical collection devices, having coated surfaces which can exhibit good frictional properties and provide a neutral surface that does not adversely affect biological materials and pharmaceutical materials in contact therewith.

2. Description of Related Technology

Traditionally, containers for chemically sensitive materials have been made from inorganic materials such as glass. Glass containers offer the advantage that they are substantially impenetrable by atmospheric gases and thus provide a product with a long shelf life. However, glass containers can be fragile and expensive to manufacture.

More recently, lighter and less expensive containers made of polymeric materials are being used in applications in which traditional glass containers were used. These polymeric containers are less susceptible to breakage, lighter, and less expensive to ship than glass containers. However, polymeric containers can be permeable to gases, permitting atmospheric gases to pass through the polymeric container to the packaged product and also permitting gases in the packaged product to escape through the polymeric container, both of which undesirably degrade the quality and shelf life of the packaged product.

Whether the container is formed from glass or polymeric material, reactivity of the interior surface of the container with the contents of the container, such as biological materials and/or drugs, can be problematic. Trace components of the glass or polymeric material and coatings on the interior of the container may migrate into the container contents, and/or components of the container contents may migrate or react with the interior surface of the container.

Also, certain devices, such as syringe barrels, require slow and controlled initiation and maintenance of sliding movement of one surface over another surface. It is well known that two stationary surfaces having a sliding relationship often exhibit sufficient resistance to initiation of movement that gradually increased force applied to one of the surfaces does not cause movement until a threshold force is reached, at which point a sudden sliding or shearing separation of the surfaces takes place. This sudden separation of stationary surfaces into a sliding relationship is herein referred to as "breakout" or "breakloose".

"Breakout force" refers to the force required to overcome static friction between surfaces of a syringe assembly that has been previously moved in a sliding relationship, but has been stationary ("parked" or not moved) for a short period of time (for example, milliseconds to hours). A less well known but important frictional force is "breakloose force", which refers to the force required to overcome static friction between surfaces of a syringe assembly that have not been previously moved in a sliding relationship or have been stationary for longer periods of time, often with chemical or material bonding or deformation of the surfaces due to age, sterilization, temperature cycling, or other processing.

Breakout and breakloose forces are particularly troublesome in liquid dispensing devices, such as syringes, used to deliver small, accurately measured quantities of a liquid by smooth incremental line to line advancement of one surface over a second surface. The problem also is encountered in devices using stopcocks, such as burets, pipets, addition funnels, and the like where careful dropwise control of flow is desired.

The problems of excessive breakout and breakloose forces are related to friction. Friction is generally defined as the resisting force that arises when a surface of one substance slides, or tends to slide, over an adjoining surface of itself or another substance. Between surfaces of solids in contact, there may be two kinds of friction: (1) the resistance opposing the force required to start to move one surface over another, conventionally known as static friction, and (2) the resistance opposing the force required to move one surface over another at a variable, fixed, or predetermined speed, conventionally known as kinetic friction.

The force required to overcome static friction and induce breakout or breakloose is referred to as the "breakout force" or "breakloose force", respectively, and the force required to maintain steady slide of one surface over another after breakout or breakloose is referred to as the "sustaining force". Three main factors, sticktion, inertia, and dimensional interference (including morphology) between the two surfaces contribute to static friction and thus to the breakout or breakloose force. The term "stick" or "sticktion" as used herein denotes the tendency of two surfaces in stationary contact to develop a degree of adherence to each other. The term "inertia" is conventionally defined as the indisposition to motion which must be overcome to set a mass in motion. In the context of the present invention, inertia is understood to denote that component of the breakout or breakloose force which does not involve adherence.

Breakout or breakloose forces, in particular the degree of sticktion, vary according to the composition and dimensional interference (related to morphology) of the surfaces. In general, materials having elasticity show greater sticktion than non-elastic materials. The length of time that surfaces have been in stationary contact with each other also influences breakout and/or breakloose forces. In the syringe art, the term "parking" denotes storage time, shelf time, or the interval between filling and discharge. Parking time generally increases breakout or breakloose force, particularly if the syringe has been refrigerated or heated during parking.

A conventional approach to overcoming breakout or breakloose has been application of a lubricant to a surface interface. Common lubricants used are silicone or hydrocarbon oils, such as mineral oils, peanut oil, vegetable oils, and the like. Such products have the disadvantage of being soluble in a variety of fluids, such as vehicles commonly used to dispense medicaments. In addition, hydrocarbon oil lubricants are subject to air oxidation resulting in viscosity changes and objectionable color development. Further, they are particularly likely to migrate from the surface to surface interface. Such lubricant migration is generally thought to be responsible for the increase in breakout or breakloose force with time in parking. As a separate issue, the lubricant can also migrate into the contained solution causing undesirable interactions with or instability of the active biological materials, drugs, pharmaceutical ingredients or excipients. This contact may occur on the surface of the silicone coated container or on the silicone droplet that has been sloughed into the bulk of the liquid contained in the syringe.

Thus, there is a need for a lubricity mechanism to overcome high breakout and breakloose forces whereby smooth transition of two surfaces from stationary contact into sliding contact can be achieved. Also, there is a need for an improved barrier coating to prevent leaching of materials from a container or seal surface into the container contents and/or from the container contents into the container or seal surface, and to prevent gas and/or water permeability in medical articles, such as syringes, tubes and medical collection devices.

SUMMARY OF THE INVENTION

In some non-limiting embodiments, the present invention provides a medical article comprising a substrate having a coating on a surface thereof, the coating comprising: (1) at least one organopolysiloxane and (2) a deposition product applied to the at least one organopolysiloxane by plasma-enhanced chemical vapor deposition of a composition comprising at least one monomer selected from the group consisting of N-vinyl pyrrolidone, vinyl acetate, ethylene oxide, alkyl acrylate, alkyl methacrylate, acrylamide, acrylic acid, and mixtures thereof.

In some non-limiting embodiments, the present invention provides a syringe barrel having a coating on an inner surface thereof, the coating comprising at least one organopolysiloxane applied to the inner surface of the syringe barrel and a deposition product applied thereon, the deposition product being prepared by plasma-enhanced chemical vapor deposition of a composition comprising at least one monomer selected from the group consisting of N-vinyl pyrrolidone, vinyl acetate, ethylene oxide, alkyl acrylate, alkyl methacrylate, acrylamide, acrylic acid, and mixtures thereof.

In some non-limiting embodiments, the present invention provides a method for coating a surface of a medical article, comprising: (a) applying a first coating comprising at least one organopolysiloxane to a surface of a substrate; and (b) applying a deposition product to at least a portion of the first coating by plasma-enhanced chemical vapor deposition of a composition comprising at least one monomer selected from the group consisting of N-vinyl pyrrolidone, vinyl acetate, ethylene oxide, alkyl acrylate, alkyl methacrylate, acrylamide, acrylic acid, and mixtures thereof.

In some non-limiting embodiments, the present invention provides a method for lubricating an interface between an inner surface of a chamber and an exterior surface of a sealing member of a medical article, comprising: (a) applying a first coating comprising at least one organopolysiloxane onto the interior surface of the chamber and/or the exterior surface of the sealing member; (b) applying a deposition product to at least a portion of the first coating by plasma-enhanced chemical vapor deposition of a composition comprising at least one monomer selected from the group consisting of N-vinyl pyrrolidone, vinyl acetate, ethylene oxide, alkyl acrylate, alkyl methacrylate, acrylamide, acrylic acid, and mixtures thereof.

BRIEF DESCRIPTION OF THE DRAWINGS

The foregoing summary, as well as the following detailed description, will be better understood when read in conjunction with the appended drawings. In the drawings.

DETAILED DESCRIPTION

Other than in the operating examples, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10. A range of "less than 5" includes all subranges below 5.

In some non-limiting embodiments, the present invention encompasses a medical article comprising a substrate having a coating on a surface thereof, the coating comprising: (1) at least one organopolysiloxane and (2) a deposition product applied to the at least one organopolysiloxane by plasma-enhanced chemical vapor deposition of a composition comprising at least one monomer selected from the group consisting of N-vinyl pyrrolidones, vinyl acetate, ethylene oxide, alkyl acrylate, alkyl methacrylate, acrylamide, acrylic acid, and mixtures thereof.

In some non-limiting embodiments, the coated surface of the medical article is a contact surface which is adapted to sealingly engage with another surface of the medical article, for example, the medical article can comprise a chamber (container) or barrel having an inner surface adapted to sealingly engage an exterior surface of a sealing member. Alternatively or additionally, the coated surface of the medical article is a contact surface which is adapted to sealingly engage with a surface of another medical article.

While not intending to be limited, the present invention now will be discussed with respect to chambers (containers) and sealing members of medical articles. The respective contact surfaces of the chamber and the sealing member can be in frictional engagement. When used in a medical article, the effects of the present invention can reduce the force required to achieve breakout, breakloose, and/or sustaining forces, whereby transition of surfaces from stationary contact to sliding contact occurs without a sudden surge. When breakout or breakloose is complete and the surfaces are in sliding contact, they slide smoothly upon application of very low sustaining force. The effect achieved by the methods of the present invention can be of long duration, and articles, such as syringes, can retain the advantages of low breakout, low breakloose, and low sustaining forces for several years. When the chamber is part of a liquid dispensing device, small highly accurate increments of liquid may be dispensed repeatedly without sudden surges. Thus, a syringe including a chamber and/or sealing member treated according to the present invention can be used to administer a medicament to a patient without the danger of surges whereby accurate control of dosage and greatly enhanced patient safety can be realized.

Another feature of the coated medical article of the present invention is that the layer comprising the deposition product can provide a stabilizing layer that can prevent biological material, such as protein or drugs, contained in the medical article or chamber from contacting or interacting with the underlying organopolysiloxane layer, preventing unfolding and aggregation of the protein and other adverse interactions between the biological material and/or drug and the organopolysiloxane.

In aqueous solutions, proteins have been shown to be preferentially hydrated in the presence of large polymers. This has been attributed to steric exclusion of large polymers like polyethylene glycols from the protein surface. While not intending to be bound by any theory, it is believed that the principle of steric exclusion in solution state to a solid-liquid interface keeps the protein from interacting with the organopolysiloxane in the present invention.

While not intending to be bound by any theory, it is believed that at least a portion of the monomer(s) deposited by plasma-enhanced CVD (and/or fragments thereof and/or polymerizates formed therefrom) reacts with at least a portion of the organopolysiloxane(s), for example by chemical crosslinking of crosslinkable components of the monomer with crosslinkable components of the organopolysiloxane to form chemical bonds therebetween, such as covalent bonds.

Alternatively or additionally, while not intending to be bound by any theory, it is believed that at least a portion of the monomer(s) (and/or fragments thereof and/or polymerizates formed therefrom) deposited by plasma-enhanced CVD diffuses into at least a portion of the organopolysiloxane(s). This diffusion is believed to be facilitated by the relatively small size of the monomer molecules, fragments of the monomer and polymerizates thereof compared to the organopolysiloxane.

In some non-limiting embodiments, this chemical reaction or diffusion can form a uniform or non-uniform gradient layer of the polymerized monomer and organopolysiloxane, with higher concentrations of the monomer/polymerizate proximate the outer surface of the coating compared to within the bulk of the coating.

In some non-limiting embodiments, the coatings of the present invention can exhibit less sub-visual particle formation in fluids stored in the chamber as compared to a similar organopolysiloxane coating without plasma-enhanced CVD deposition of the monomer(s).

As discussed above, in some non-limiting embodiments, the present invention encompasses medical articles. In some non-limiting embodiments, the medical article comprises a substrate having a contact surface in frictional engagement with a contact surface of another portion of the medical article, or with a contact surface of another medical article. As used herein, "medical article" means an article of manufacture or device that can be useful for medical treatment. Non-limiting examples of medical articles include articles selected from the group consisting of a syringe assembly, drug cartridge, needleless injector, liquid dispensing device, liquid metering device, sample collection tube or plate assembly, catheter, and vial. In some non-limiting embodiments, the medical article is a syringe assembly comprising a syringe chamber or barrel (for receiving, for example, water, saline, a medicament, or a biological material, such as a protein) and a sealing member.

While not intending to be limited, the present invention now will be discussed with respect to chambers (containers) and sealing members of medical articles.

In some non-limiting embodiments, the chamber is selected from the group consisting of a syringe barrel, liquid container, and tube. The chamber can be formed from glass, metal, ceramic, plastic, rubber or combinations thereof. In some non-limiting embodiments, the chamber is prepared from Type I borosilicate glass. In some non-limiting embodiments, the chamber is prepared from one or more olefinic polymers, such as polyethylene, polypropylene, poly(1-butene), poly(2-methyl-1-pentene), and/or cyclic polyolefins. For example, the polyolefin can be a homopolymer or a copolymer of an aliphatic monoolefin, the aliphatic monoolefin preferably having about 2 to 6 carbon atoms, such as polypropylene. In some non-limiting embodiments, the polyolefin can be basically linear, but optionally may contain side chains such as are found, for instance, in conventional, low density polyethylene. In some non-limiting embodiments, the polyolefin is at least 50% isotactic. In other non-limiting embodiments, the polyolefin is at least about 90% isotactic in structure. In some non-limiting embodiments, syndiotactic polymers can be used. In some embodiments, cyclic polyolefins can be used. Non-limiting examples of suitable cyclic polyolefins include dicyclopentadiene (DCP), norbornene, tetracyclododecene (TCD), alternating, random or block ethylene/norbonanediyl units, or other polymeric type units such as are disclosed in U.S. Pat. Nos. 6,525,144, 6,511,756, 5,599,882, and 5,034,482 (each of Nippon Zeon), U.S. Pat. Nos. 7,037,993, 6,995,226, 6,908,970, 6,653,424 and 6,486,264 (each of Zeon Corp.), U.S. Pat. Nos. 7,026,401, and 6,951,898 (Ticona), U.S. Pat. No. 6,063,886 (Mitsui Chemicals), U.S. Pat. Nos. 5,866,662, 5,856,414, 5,623,039 and 5,610,253 (Hoechst), U.S. Pat. Nos. 5,854,349, and 5,650,471 (Mitsui Petrochemical and Hoechst) and as described in "Polycyclic olefins", process Economics Program (July 1998) SRI Consulting, each of the foregoing references being incorporated by reference herein. Non-limiting examples of suitable cyclic polyolefins include Apel™ cyclic polyolefins available from Mitsui Petrochemical, Topas™ cyclic polyolefins available from Ticona Engineering Polymers, Zeonor™ or Zeonex™ cyclic polyolefins available from Zeon Corporation, and cyclic polyolefins available from Promerus LLC.

The polyolefin can contain a small amount, generally from about 0.1 to 10 percent, of an additional polymer incorporated into the composition by copolymerization with the appropriate monomer. Such copolymers may be added to the composition to enhance other characteristics of the final composition, and may be, for example, polyacrylate, polystyrene, and the like.

In some non-limiting embodiments, the chamber may be constructed of a polyolefin composition which includes a radiation stabilizing additive to impart radiation stability to the chamber, such as a mobilizing additive which contributes to the radiation stability of the chamber, such as for example those disclosed in U.S. Pat. Nos. 4,959,402 and 4,994,552, assigned to Becton, Dickinson and Company and both of which are incorporated herein by reference.

In some non-limiting embodiments, the chamber or container of the present invention is a blood collection device. The blood collection device can be either an evacuated blood collection tube or a non-evacuated blood collection tube. The blood collection tube can be made of polyethylene terephthalate, polypropylene, polycarbonate, polycycloolefin, polyethylene naphthalate or copolymers thereof.

The dimensions, e.g., inner and outer diameter, length, wall thickness, etc. of the chamber can be of any size desired. For example, for a one ml volume syringe barrel, the inner diameter of the barrel is about 0.25 inches (6.30 mm) and the length is about 2.22 inches (56.4 mm). For a plastic Sterifill 20 ml volume syringe barrel, the inner diameter of the barrel is about 0.75 inches (19.05 mm) and the length is about 3.75 inches (95.3 mm). Generally, the inner diameter can range from about 0.25 inches (6.35 mm) to about 10 inches (254 mm), or about 0.25 inches (6.35 mm) to about 5 inches (127 mm), or any value therebetween. Other useful blood collection devices include Hypak™ syringes and Sterifill™ syringes, which are available from Becton, Dickinson and Company.

The other component of the medical article in contact with the chamber is the sealing member. The sealing member can be formed from any elastomeric or plastic material. Elastomers are used in many important and critical applications in medical devices and pharmaceutical packaging. As a class of materials, their unique characteristics, such as flexibility, resilience, extendability, and sealability, have proven particularly well suited for products such as catheters, syringe tips, drug vial articles, tubing, gloves, and hoses. Three primary synthetic thermoset elastomers typically are used in medical applications: polyisoprene rubber, silicone rubber, and butyl rubber. Of the three rubbers, butyl rubber has been the most common choice for articles due to its high cleanness and permeation resistance which enables the rubber to protect oxygen- and water-sensitive drugs.

Suitable butyl rubbers useful in the present invention include copolymers of isobutylene (about 97-98%) and isoprene (about 2-3%). The butyl rubber can be halogenated with chlorine or bromine. Suitable butyl rubber vulcanizates can provide good abrasion resistance, excellent impermeability to gases, a high dielectric constant, excellent resistance to aging and sunlight, and superior shock-absorbing and vibration-damping qualities to articles formed therefrom. Non-limiting examples of suitable rubber stoppers include those available from West Pharmaceuticals, American Gasket Rubber, Stelmi, and Helvoet Rubber & Plastic Technologies BV.

Other useful elastomeric copolymers include, without limitation, thermoplastic elastomers, thermoplastic vulcanizates, styrene copolymers such as styrene-butadiene (SBR or SBS) copolymers, styrene-ethylene/butylene-styrene (SEBS) copolymers, styrene-ethylene/propylene-styrene (SEPS) copolymers, styrene-isoprene (SIS) block polymers or styrene-isoprene/butadiene (SIBS), in which the content of styrene in the styrene block copolymer ranges from about 10% to about 70%, and preferably from about 20% to about 50%. Non-limiting examples of suitable styrene-butadiene stoppers are available from Firestone Polymers, Dow, Reichhold, Kokoku Rubber Inc., and Chemix Ltd. Other suitable thermoplastic elastomers are available from GLS, Tecknor Apex, AES, Mitsubishi and Solvay Engineered Polymers, for example. The elastomer composition can include, without limitation, antioxidants, UV resistance additives and/or inorganic reinforcing agents to preserve the stability of the elastomer composition.

In some non-limiting embodiments, the sealing member can be a stopper, O-ring, V-ring, plunger tip, or piston, for example. Syringe plunger tips or pistons typically are made of a compressible, resilient material such as rubber, because of the rubber's ability to provide a seal between the plunger and interior housing of the syringe. Syringe plungers, like other equipment used in the care and treatment of patients, have to meet high performance standards, such as the ability to provide a tight seal between the plunger and the barrel of the syringe.

Figure 1A:
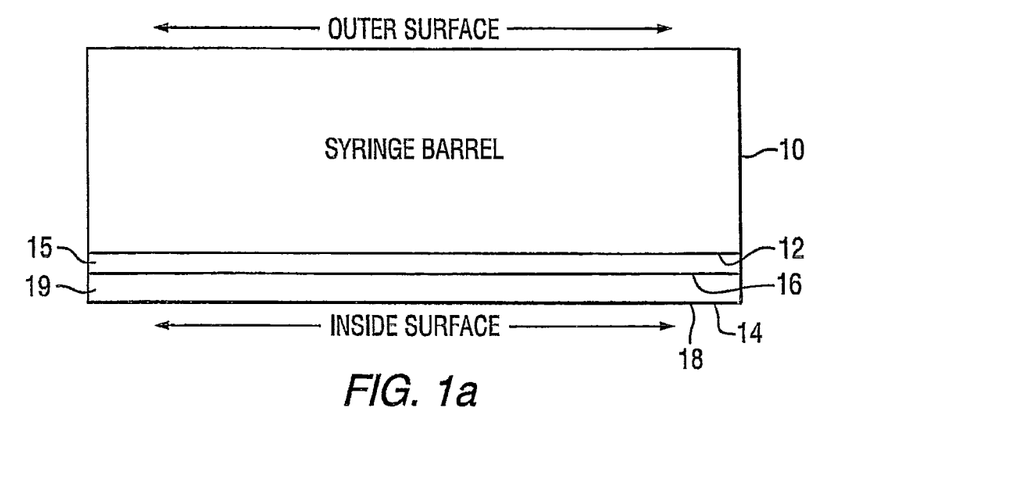
FIG. 1a is a schematic of a portion of a syringe barrel having a coating on an inner surface thereof, according to the present invention.

Referring now to FIG. 1a, there is shown a schematic drawing of a portion of a chamber or syringe barrel 10, including an inner surface 12. The coating 14 is applied to at least a portion of the inner surface 12 of the syringe barrel 10 and/or sealing member (not shown). In some non-limiting embodiments, the chamber is coated with the coating described below and the sealing member is uncoated or coated with a polydimethylsiloxane coating or another coating. In other non-limiting embodiments, the sealing member is coated with the coating described below and the chamber is uncoated or coated with a polydimethylsiloxane coating or another coating. In other non-limiting embodiments, both the chamber and sealing member are coated with coatings as described below. Methods for coating the surface(s) are discussed in detail below.

First, the chamber and/or sealing member are coated with a coating prepared from a composition comprising one or more organopolysiloxane(s). In some non-limiting embodiments, the organopolysiloxane has a viscosity ranging from about 100 to about 1,000,000 centistokes (cst), prior to any curing step, or from about 1,000 cst to about 100,000 cst, or from about 1,000 cst to about 15,000 cst. In other non-limiting embodiments, the organopolysiloxane has a viscosity of about 100,000 cst. The viscosity can be measured using a Brookfield DV II+ viscometer using a suitable spindle, such as a #4 spindle, at a temperature of about 25° C.

In some non-limiting embodiments, the organopolysiloxane comprises an alkyl-substituted organopolysiloxane, for example as is represented by the following structural Formula (I):

wherein each R is an independently selected alkyl group, such as methyl or ethyl, and Z is about 30 to about 4,500. In some non-limiting embodiments, the organopolysiloxane of Formula (I) can be represented by the following structural Formula (II):

(II)

wherein Z can be as above, or for example can be about 300 to about 2,000, about 300 to about 1,800, or about 300 to about 1,350.

In some non-limiting embodiments, the organopolysiloxane is a polydimethylsiloxane, for example DOW CORNING® polydimethylsiloxanes available from Dow Corning Corp. of Midland, Mich., having a viscosity ranging from about 1,000 to about 12,500 cst at a temperature of about 25° C., such as DOW CORNING® polydimethylsiloxane 360 linear polydimethylsiloxane, or NUSIL polydimethylsiloxanes available from NuSil Technology LLC of Carpinteria, Calif., having a viscosity ranging from about 100 to about 1,000,000 cst at 25° C.

In other embodiments, the organopolysiloxane comprises one or more curable or reactive functional groups, such as alkenyl groups. As used herein, the term "cure" as used in connection with a composition, i.e., a "cured composition" or a "cured coating" shall mean that at least a portion of the crosslinkable components which form the composition are at least partially crosslinked. As used herein, the term "curable", as used in connection with a component of the composition, means that the component has functional groups capable of being crosslinked, for example, alkenyl groups such as vinyl groups. In certain embodiments of the present invention, the crosslink density of the crosslinkable components, i.e., the degree of crosslinking, ranges from 5% to 100% of complete crosslinking. One skilled in the art will understand that the presence and degree of crosslinking, i.e., the crosslink density, can be determined by a variety of methods, such as dynamic mechanical thermal analysis (DMTA). This method determines the glass transition temperature and crosslink density of free films of coatings or polymers. These physical properties of a cured material are related to the structure of the crosslinked network.

In some non-limiting embodiments, the organopolysiloxane comprises at least one alkenyl group. Each alkenyl group can be independently selected from the group consisting of vinyl, allyl, propenyl, butenyl, pentenyl, hexenyl, heptenyl, octenyl, nonenyl, and decenyl. One skilled in the art would understand that the organopolysiloxane can comprise one or more of any of the above types of alkenyl groups and mixtures thereof. In some non-limiting embodiments, at least one alkenyl group is vinyl. Higher alkenyl or vinyl content provides more efficient crosslinking.

In some non-limiting embodiments, the organopolysiloxane can be represented by the following structural Formulae (III) or (IV):

(III)

(IV)

wherein R is alkyl, haloalkyl, aryl, haloaryl, cycloalkyl, silacyclopentyl, aralkyl, and mixtures thereof; X is about 60 to about 1,000, preferably about 200 to about 320; and y is about 3 to about 25. Copolymers and mixtures of these polymers also are contemplated.

Non-limiting examples of useful vinyl functional organopolysiloxanes include: vinyldimethylsiloxy terminated polydimethylsiloxanes; trimethylsiloxy terminated vinylmethyl, dimethylpolysiloxane copolymers; vinyldimethylsiloxy terminated vinylmethyl, dimethylpolysiloxane copolymers; divinylmethylsiloxy terminated polydimethylsiloxanes; vinyl, n-butylmethyl terminated polydimethylsiloxanes; and vinylphenylmethylsiloxy terminated polydimethylsiloxanes.

In some embodiments, a mixture of siloxane polymers selected from those of Formulae II, III and/or IV can be used. For example, the mixture can comprise two different molecular weight vinyldimethylsiloxy terminated polydimethylsiloxane polymers, wherein one of the polymers has an average molecular weight of about 1,000 to about 25,000 and preferably about 16,000, and the other polymer has an average molecular weight of about 30,000 to about 71,000 and preferably about 38,000. Generally, the lower molecular weight siloxane can be present in amounts of about 20% to about 80%, such as about 60% by weight of this mixture; and the higher molecular weight siloxane can be present in amounts of about 80% to about 20%, such as about 40% by weight of this mixture.

Another non-limiting example of a suitable vinyl functional organopolysiloxane is (7.0-8.0% vinylmethylsiloxane)-dimethylsiloxane copolymer, trimethylsiloxy terminated, such as VDT-731 vinylmethylsiloxane copolymer which is commercially available from Gelest, Inc. of Morrisville, Pa.

In some non-limiting embodiments, the organopolysiloxane can comprise at least two polar groups. Each polar group can be independently selected from the group consisting of acrylate, methacrylate, amino, imino, hydroxy, epoxy, ester, alkyloxy, isocyanate, phenolic, polyurethane oligomeric, polyamide oligomeric, polyester oligomeric, polyether oligomeric, polyol, and carboxypropyl groups. One skilled in the art would understand that the organopolysiloxane can comprise one or more of any of the above polar groups and mixtures thereof.

In some embodiments, the polar groups are acrylate groups, for example, acryloxypropyl groups. In other embodiments, the polar groups are methacrylate groups, such as methacryloxypropyl groups. The organopolysiloxane having polar groups can further comprise one or more alkyl groups and/or aryl groups, such as methyl groups, ethyl groups, or phenyl groups. Non-limiting examples of such organopolysiloxanes include [15-20% (acryloxypropyl)methylsiloxane]-dimethylsiloxane copolymer, such as UMS-182 acrylate functional siloxane, which is available from Gelest, Inc. of Morrisville, Pa., and SILCOLEASE® PC970 acrylated silicone polymer, which is available from Rhodia-Silicones.

In other non-limiting embodiments, such an organopolysiloxane can be represented by the Formula (V):

wherein $R_1$ is selected from the group consisting of acrylate, methacrylate, amino, imino, hydroxy, epoxy, ester, alkyloxy, isocyanate, phenolic, polyurethane oligomeric, polyamide oligomeric, polyester oligomeric, polyether oligomeric, polyol, carboxypropyl, and fluoro groups; and R.sub.2 is alkyl, n ranges from 2 to 4, and x is an integer sufficient to give the lubricant a viscosity of about 100 to 1,000,000 cst.

While not wishing to be bound by any theory, it is believed that the polar siloxanes may help reduce the coefficient of friction between the engaged surfaces. Also, after irradiation, it is believed that the viscosity of the polar siloxane may increase and improve the adhesion of the coating to substrate.

In some non-limiting embodiments, the organopolysiloxane can further comprise one or more fluoro groups, such as—F or fluoroalkyl groups such as trifluoromethyl groups. Other useful organopolysiloxanes include polyfluoroalkylmethyl siloxanes and fluoroalkyl, dimethyl siloxane copolymers.

In some non-limiting embodiments, the composition can further comprise one or more cyclic siloxane(s), for example, octamethylcyclotetrasiloxane and/or decamethylcyclopentasiloxane.

In some non-limiting embodiments, the organopolysiloxane can be represented by the following structural Formula (VI):

$$(R)_3SiO(SiO)_zSi(R)_3 \quad \overset{R}{\underset{R}{|}} \qquad (VI)$$

wherein R is haloalkyl, aryl (such as phenyl), haloaryl, cycloalkyl, silacyclopentyl, aralkyl and mixtures thereof; and Z is about 20 to about 1,800.

In some non-limiting embodiments, the organopolysiloxane comprises at least two pendant hydrogen groups. Non-limiting examples of suitable organopolysiloxanes comprising at least two pendant hydrogen groups include organopolysiloxanes having pendant hydrogen groups along the polymer backbone or terminal hydrogen groups. In some non-limiting embodiments, the organopolysiloxane can be represented by the following structural Formulae (VII):

wherein p is about 8 to about 125, for example, about 30.

In other non-limiting embodiments, the organopolysiloxane can be represented by the following structural Formula (VIII):

$$HMe_2SiO(Me_2SiO)_pSiMe_2H \qquad (VIII)$$

wherein p is about 140 to about 170, for example, about 150 to about 160. A mixture of these polymers can be used comprising two different molecular weight materials. For example, about 2% to about 5% by weight of the mixture of a trimethylsiloxy terminated polymethylhydrosiloxane having an average molecular weight of about 400 to about 7,500, for example about 1900, can be used in admixture with about 98% to about 95% of a dimethylhydro siloxy-terminated polydimethylsiloxane having an average molecular weight of about 400 to about 37,000 and preferably about 12,000. Non-limiting examples of useful organopolysiloxanes comprising at least two pendant hydrogen groups include dimethylhydro terminated polydimethylsiloxanes; methylhydro, dimethylpolysiloxane copolymers; dimethylhydrosiloxy terminated methyloctyl dimethylpolysiloxane copolymers; and methylhydro, phenylmethyl siloxane copolymers.

In some non-limiting embodiments, the composition comprises hydroxy functional siloxanes, for example a hydroxy functional siloxane comprising at least two hydroxyl groups, such as for example:

wherein $R_2$ is alkyl, n ranges from 0 to 4, and x is an integer sufficient to give the lubricant a viscosity of about 100 to 1,000,000 cst. In some embodiments, moisture-curable siloxanes which have moisture-curing character as a result of functionality include siloxanes having functional groups such as: alkoxy; aryloxy; oxime; epoxy; —OCCR; N,N-dialkylamino; N,N-dialkylaminoxy; N-alkylamido; —O—NH—C(O)—R; —O—C(=NCH$_3$)—NH—CH$_3$; and —O—C(CH$_3$)=CH$_2$, wherein R is H or hydrocarbyl. As used herein, "moisture-curable" means that the siloxane is curable at ambient conditions in the presence of atmospheric moisture.

Mixtures of one or more of the organopolysiloxanes discussed above can be used in the present invention.

In some non-limiting embodiments, the organopolysiloxane comprises about 90 to about 100 weight percent of the composition. In other embodiments, the organopolysiloxane comprises about 95 to about 100 weight percent of the composition. In other embodiments, the organopolysiloxane comprises 100 weight percent of the composition.

In some non-limiting embodiments, the composition further comprises a catalytic amount of a catalyst for promoting crosslinking of crosslinkable groups of the organopolysiloxane(s). Non-limiting examples of suitable catalysts for promoting ultraviolet radiation cure include any suitable photoinitiator which is capable of initiating polymerization of the reactive silicone polymer upon exposure to UV light. Non-limiting examples of useful UV light-induced polymerization photoinitiators include ketones such as benzyl and benzoin, and acyloins and acyloin ethers, such as alpha-hydroxy ketones. Non-limiting examples of available products include IRGACURE 184 (1-hydroxycyclohexyl phenyl ketone), IRGACURE 907 (2-methyl-1-[4-(methylthio)phenyl]-2-(4-morpholinyl)-1-propanone), IRGACURE 369 (2-benzyl-2-N,N-dimethylamino-1-(4-morpholinophenyl)-1-butanone), IRGACURE 500 (the combination of 50% 1-hydroxy cyclohexyl phenyl ketone and 50% benzophenone), IRGACURE 651 (2,2-dimethoxy-1,2-diphenylethan-1-one), IRGACURE 1700 (the combination of 25% bis(2,6-dimethoxybenzoyl-2, 4-, 4-trimethyl pentyl)phosphine oxide and 75% 2-hydroxy-2-methyl-1-phenyl-propan-1-one), DAROCUR 1173 (2-hydroxy-2-methyl-1-phenyl-propan-1-one), and DAROCUR 4265 (the combination of 50% 2,4,6-trimethylbenzoyldiphenyl-phosphine oxide and 50% 2-hydroxy-2-methyl-1-phenyl-propan-1-one), all of which are available from CIBA Corp., Tarrytown, N.Y.; and SARCURE SR-1121 (2-hydroxy-2-methyl-1-phenyl propanone) and ESACURE KIP-100F (a mixture of polymeric photoinitiators in 2-hydroxy-2-methyl-1-phenyl-propan-1-one), both of which are available from Sartomer, Inc. of Exton, Pa. Of course, mixtures of different photoinitiators may also be used. The photoinitiator is desirably in a liquid form to ensure appropriate mixing and distribution within the composition, although solid photoinitiators may also be used, provided that they are soluble in organopolysiloxane to provide the composition as a homogeneous fluid. The photoinitiator should be present in an amount sufficient to provide the desired rate of photopolymerization, dependent in part on the light source and the extinction coefficient of the photoinitiator. Typically, the photoinitiator components will be present at a total weight of about 0.01 to about 10%, more preferably from about 0.1 to about 5%, based on the total weight of the composition.

Non-limiting examples of suitable catalysts for promoting heat cure include platinum or rhodium group metal catalysts, such as Karstedt catalyst $Pt_2\{[(CH_2\!=\!CH)Me_2Si]_2O\}_3$ or peroxide catalysts, such as dicumyl peroxide The catalyst can be present in an amount ranging from about 0.001 to about 0.05 weight percent of the composition.

The components of the composition can be formulated in a single composition or two compositions that are mixed prior to application, for example, to separate a catalyst from crosslinkable components until shortly before application. A non-limiting example of a suitable two component composition is a two-part LSR silicone composition commercially available from GE Silicones.

Application of a coating 15 to the inner surface 12 of the syringe barrel 10 or outer surface of the sealing member may be accomplished by any suitable method, as, for example, dipping, brushing, spraying, and the like. The composition may be applied neat or it may be applied in a solvent, such as low molecular weight silicone, non-toxic chlorinated or fluorinated hydrocarbons, for example, 1,1,2-trichloro-1,2,2-trifluoroethane, Freon or conventional hydrocarbon solvents such as alkanes, toluene, petroleum ether, and the like where toxicology is not considered important. The solvent is subsequently removed by evaporation. Useful methods for applying the surface lubricant are by spraying or dipping the syringe barrel into a solution, about 4% by weight, of the surface lubricant in a solvent such as chloroform, dichloromethane or preferably a chlorofluorocarbon, such as FREON™ TF.

The surface lubricant may optionally be crosslinked by oxidative treatment and/or radiation as described in U.S. Pat. Nos. 4,452,679, 4,767,414, 4,822,632, U.S. Patent Publication 2008/0071228, incorporated by reference herein. The coating 15 can be partially or fully crosslinked after application or partially crosslinked to attach to the substrate, and then fully crosslinked at a later time.

The coating 15 may be of any convenient thickness. The thickness will be determined by such factors as the quantity applied, viscosity of the lubricant, and the temperature of application. For reasons of economy, the coating preferably is applied as thinly as practical, since no significant advantage is gained by thicker coatings. The exact thickness of the coating 15 does not appear to be critical and very thin coatings, i.e., less than one or two microns, can exhibit effective lubricating properties. While not necessary for operability, it is desirable that the thickness of the coating be substantially uniform throughout. The thickness of the coating layer can range from about 50 nm to about 2 μm, or about 500 nm to about 1000 nm, or about 1000 nm to about 2 μm.

As discussed above, a deposition product 19 is applied to the outer surface 16 of the organopolysiloxane coating 15 by plasma-enhanced chemical vapor deposition (PECVD) of a composition as discussed below.

The term "chemical vapor deposition" as used herein means a process which transforms gaseous molecules or radicals into solid material in the form of thin film or powder on the surface of a substrate. PECVD is a process used to deposit thin films from a gas state (vapor) to a solid state on a substrate. Chemical reactions are involved in the process, which occur after creation of a plasma of the reacting gases. The plasma is generally created by $R_f$ (AC) frequency or DC discharge between two electrodes, the space between which is filled with the reacting gases.

Suitable methods for PECVD are well known to those skilled in the art. For example, the coating layer can be deposited by PECVD in a manner described in A. Millela et al., "Deposition Mechanism of Nanostructured Thin Films from Tetrafluoroethylene Glow Discharges", *Pure App. Chem.*, Vol. 77, No. 2, pp. 399-414 (2005), incorporated by reference herein. The deposition product 19 can be deposited by a single PECVD application, or by applying multiple layers using multiple PECVD applications. If multiple depositions are used, the monomer(s) included in each deposition can be the same as or different from the monomer(s) used in subsequent depositions.

Figure 2:
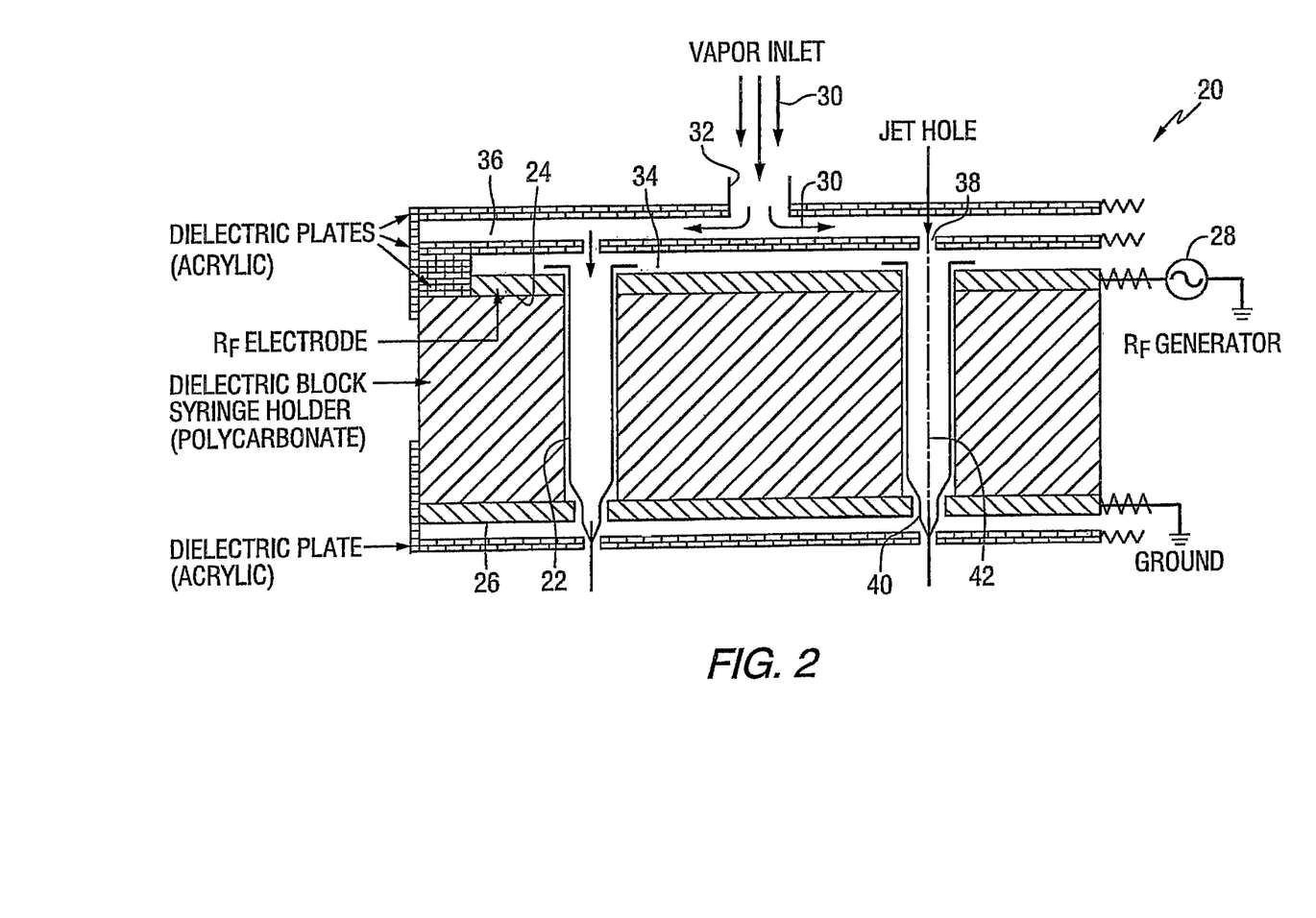
FIG. 2 is a schematic of a plasma-enhanced CVD apparatus useful to apply the coating of the present invention.

For example, the PECVD process can be conducted using a vacuum plasma system that is comprised of a 30 cm diameter by 55 cm high chamber pumped by a turbo molecular pump backed by a two-stage rotary pump. Referring now to FIG. 2, there is shown a portion of a suitable electrode system, indicated generally as 20. The electrode system 20 holds a matrix of syringe barrels 22 between two electrodes 24, 26. The bottom electrode 26 is grounded and the top electrode 24 is energized by a radio frequency (Rf) generator 28. Monomer gases 30 are metered through a mass flow controller (not shown) into an inlet 32 in the electrode assembly 34 where a manifold 36 distributes the monomer gas 30 to jet holes 38 positioned above the open mouth of each individual barrel 22. The monomer gas 30 is injected into the barrel 22 in a manner that ensures mixing and allows the monomer gas 30 to reach the bottom 40 of the barrels 22. The Rf field generated by the electrodes 24, 26 is directed along the axis 42 of the barrels 22, ionizing the monomer gas 22 inside and initiating the polymerization reaction. The sequence of the process is to load and seal the chamber, pump to a base pressure of about 1 mTorr, introduce the process gas at a pressure of about 80 to 200 mTorr, ignite the Rf plasma for a period of about 1 to 120 seconds, vent the chamber to atmosphere and remove the coated barrels. Generally, the frequency can range from about 0.1 to about 100 MHz, the power can range from about 5 to about 100 W, and the temperature of the monomer gas and substrate can be about room temperature (about 25° C.).

The composition to be deposited by PECVD comprises at least one monomer selected from the group consisting of N-vinyl pyrrolidone, vinyl acetate, ethylene oxide, alkyl acrylate, alkyl methacrylate, acrylamide, acrylic acid, and mixtures thereof.

Non-limiting examples of suitable alkyl acrylates include methyl acrylate, ethyl acrylate, butyl acrylate, and mixtures thereof. Non-limiting examples of suitable alkyl methacrylates include methyl methacrylate, ethyl methacrylate, butyl methacrylate, and mixtures thereof. If a mixture of monomers is used, the molar ratio of selected monomers can range from 1:10 to 10:1, as desired.

The monomers and their fragments are at least partially polymerized during deposition, and can react with each other to form polymerizates, or can react with the organopolysiloxane. For example, deposition of N-vinyl pyrrolidone can form polyvinyl pyrrolidone, deposition of vinyl acetate can form polyvinyl acetate, deposition of ethylene oxide can form polyethylene glycol and/or polyethylene oxide, deposition of (meth)acrylate can form poly(meth)acrylates, deposition of acrylamide can form polyacrylamides, and deposition of acrylic acid can form polyacrylic acid. Mixtures of monomers can form mixed polymerizates. The polymers can be formed by radical polymerization of the monomer(s) to form covalent bonds.

In some non-limiting embodiments, one or more carrier gases, such as argon or hydrogen, can be used to facilitate deposition of the monomer/polymer.

The deposition time will depend on the flow rate, activation efficiency and targeted thickness of the coating. Typical deposition times can range from seconds to hours. Very fast deposition times are desirable. The thickness of the deposition product 19 generally can range from about 1 nm to about 5 microns, for example.

Figure 1B:
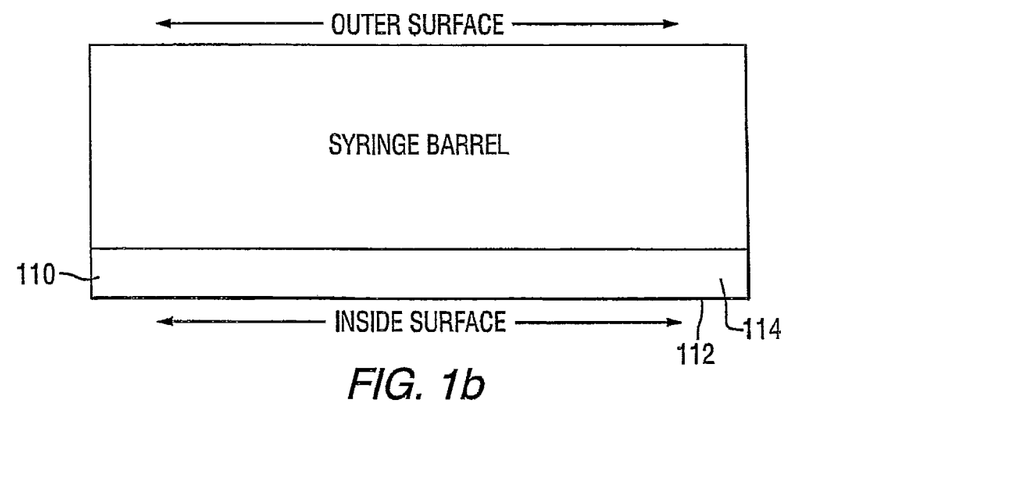
FIG. 1b is a schematic of a portion of a syringe barrel having a coating on an inner surface thereof, according to the present invention.

As discussed above, in some non-limiting embodiments, the deposition product 19 can form a separate layer over the organopolysiloxane layer having a well-defined interface, as shown in FIG. 1a. In other non-limiting embodiments, the deposition product reacts with a portion of the organopolysiloxane and/or diffuses into the organopolysiloxane coating to form a uniform or non-uniform gradient, wherein the concentration of the deposition product is higher at the outer surface 112 of the organopolysiloxane coating 110 than within the bulk 114 of the organopolysiloxane coating 110, as shown in FIG. 1b.

In some non-limiting embodiments, the outer surface 18 of the coated articles are washed with water after deposition. The water washing can be conducted at room temperature (about 25° C.) using a mildly pressurized water jet.

In some non-limiting embodiments, the coated articles are subjected to a sterilization treatment. Many sterilization techniques are available today to sterilize medical devices to eliminate living organisms such as bacteria, yeasts, mold, and viruses. Commonly used sterilization techniques used for medical devices include autoclaving, ethylene oxide (EtO) or gamma irradiation, as well as more recently introduced systems that involve low-temperature gas plasma and vapor phase sterilants. One common sterilization technique is steam sterilization or autoclaving, which is a relatively simple process that exposes an article, for example, to saturated steam at temperatures of over 120° C. for a minimum of twenty minutes at a pressure of about 120 kPa. The process is usually carried out in a pressure vessel designed to withstand the elevated temperature and pressure to kill microorganisms by destroying metabolic and structural components essential to their replication.

The mating contact surface of the other component (not coated according to the present invention discussed above) can be coated with a coating of the present invention as described above, or with a conventional siloxane or other oil coating as described above. The surface lubricant can be conventional silicone oil (organopolysiloxane) of viscosity about 100 to about 1,000,000, about 100 to about 60,000, or about 1,000 to about 12,500 cSt, evaluated using a Brookfield DV II+ viscometer using a #4 spindle at a temperature of about 25° C. The surface lubricating layer may be applied by any conventional method, as described above. The surface lubricant may optionally be lightly crosslinked by oxidative treatment and/or radiation.

In some non-limiting embodiments, the present invention provides a method for coating a surface of a medical article, comprising: (a) applying a first coating comprising at least one organopolysiloxane to a surface of a substrate; and (b) applying a deposition product to at least a portion of the first coating by plasma-enhanced chemical vapor deposition of a composition comprising at least one monomer selected from the group consisting of N-vinyl pyrrolidone, vinyl acetate, ethylene oxide, alkyl acrylate, alkyl methacrylate, acrylamide, acrylic acid, and mixtures thereof, the details of the method being described above.

In some non-limiting embodiments, the present invention provides a method for lubricating an interface between an inner surface of a chamber and an exterior surface of a sealing member of a medical article, comprising: (a) applying a first coating comprising at least one organopolysiloxane onto the interior surface of the chamber and/or the exterior surface of the sealing member; (b) applying a deposition product to at least a portion of the first coating by plasma-enhanced chemical vapor deposition of a composition comprising at least one monomer selected from the group consisting of N-vinyl pyrrolidone, vinyl acetate, ethylene oxide, alkyl acrylate, alkyl methacrylate, acrylamide, acrylic acid, and mixtures thereof, the details of the method being described above.

The present invention is more particularly described in the following examples, which are intended to be illustrative only, as numerous modifications and variations therein will be apparent to those skilled in the art.

EXAMPLES

Example A

One ml long Hypak™ syringe barrels (available from Becton, Dickinson and Company) were coated on the interior of the barrel with a coating according to the present invention. Silicone was applied to the syringe by rinsing the syringe with a 2% W/V solution of DOW CORNING® 360 (1000 cst) polydimethylsiloxane in freon. Next, a coating was deposited onto the outer surface of the polysiloxane by PECVD. The deposition apparatus consisted of a block of non-conducting material bounded on the top and bottom by aluminum plates that functioned as the electrodes, the top electrode being the $R_f$ electrode and the bottom being the ground, as shown in FIG. 2. The syringes are laid out in an six by six configuration but without any holes where the four innermost syringes would otherwise be, to accommodate a total of 32 syringes. The N-vinyl pyrrolidone monomer was drawn into the vacuum chamber through the vapor inlet under vacuum and directed into the syringes by the jet holes in the dielectric plate placed above the $R_f$ electrode. The treatment parameters are listed below: Monomer flow rate: 1 to 2 standard cubic centimeters per minute (sccm); Pressure: 40 mTorr (regulated by pump throttling) decreasing to 23 mTorr over the treatment period; Treatment period: 15 seconds; Frequency: 19 MHz; and Net Power: 30 to 36 W (range).

The characteristics of a sample coated syringe barrel were as follows:

TABLE 1

PDMS-PVP Surface Characteristics:

| Syringe Position | Composition | | | | | | Thickness (nm) |
|---|---|---|---|---|---|---|---|
| | % Si | % Na | % S | % C | % N | % O | |
| Tip | 17.6 ± 6.1 | 0.7 | 0.0 | 53.1 ± 8.8 | 5.3 ± 1.3 | 22.9 ± 3.7 | 149.5 ± 75.2 |
| Middle | 20.1 ± 4.7 | 0.0 | 0.0 | 53.1 ± 8.8 | 4.1 ± 1.4 | 22.7 ± 5.6 | 321.7 ± 218.7 |
| Flange | 21.6 ± 2.8 | 0.0 | 0.0 | 52.0 ± 2.7 | 3.3 ± 0.9 | 23.9 ± 1.9 | 248.0 |

Figure 3:
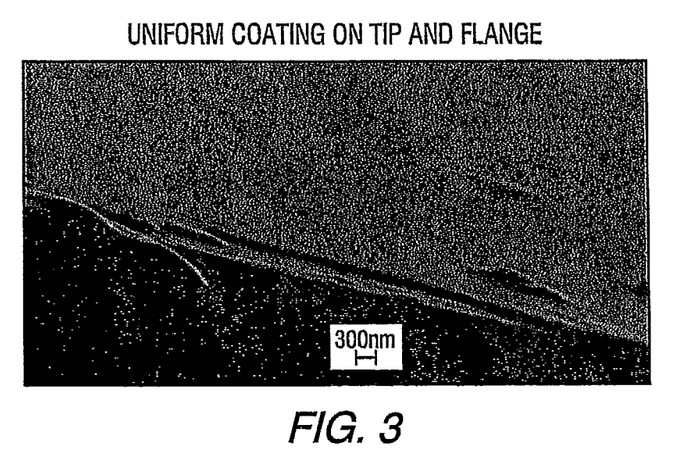
FIG. 3 is a scanning electron microscopy (SEM) photomicrograph of a portion of a syringe barrel tip and flange coated according to the present invention.
Figure 4:
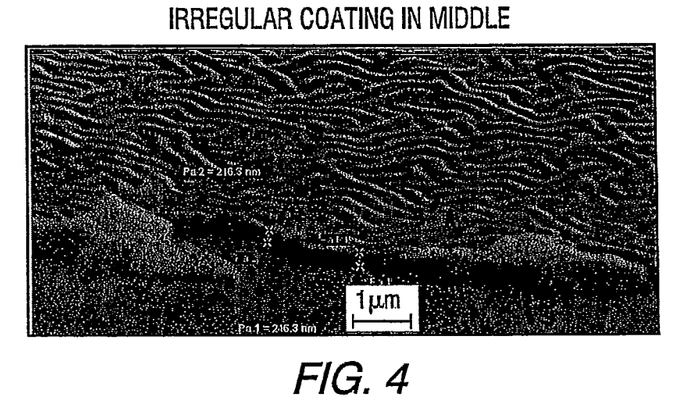
FIG. 4 is a scanning electron microscopy (SEM) photomicrograph of a middle portion of a syringe barrel coated according to the present invention.

Compare with Polydimethylsiloxane composition: 28% C, 33% Si, 38% O & PVP composition: 70% C, 15% O & 13% N FIG. 3 is a scanning electron microscopy (SEM) photomicrograph of a portion of the coated interior of the syringe barrel tip and flange, showing a generally smooth, uniform coating surface. FIG. 4 is a scanning electron microscopy (SEM) photomicrograph of a middle portion of the coated interior of the syringe barrel, showing an irregular coating surface in the middle of the syringe barrel.

Figure 5:
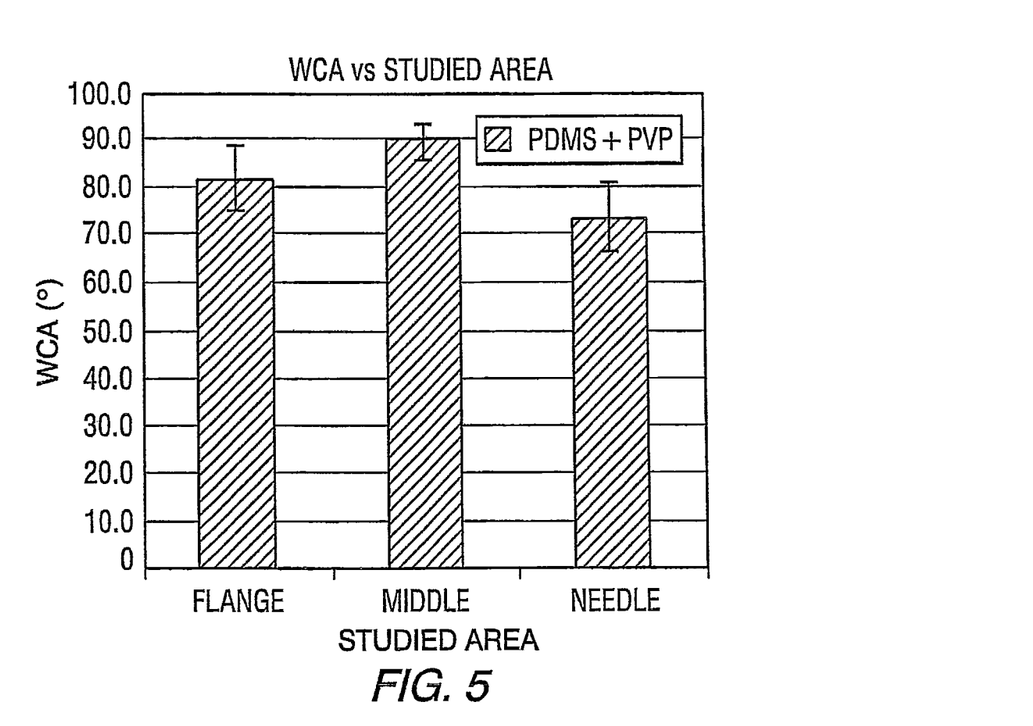
FIG. 5 is a graph of water contact angle (WCA) in degrees over a predetermined area for a syringe barrel according to the present invention.

FIG. 5 is a graph of water contact angle (WCA) in degrees over a predetermined area of one of the sample syringes prepared above. The water contact angle was measured using a goniometer. As shown in FIG. 5, the water contact angle was higher in the middle of the syringe than near the needle area or flange area. The WCA for a polydimethylsiloxane coated syringe barrel was about 112°. The WCA for a polyvinylpyrrolidone-coated syringe barrel was about 35°. The WCA for a syringe coated with polydimethylsiloxane and polyvinylpyrrolidone according to the present invention was about 80°±10°, as shown in FIG. 5. Along the length of the syringe, the coating thickness was fairly uniform. Also, the hydrophilic/lipophilic properties of the coating were fairly uniform.

Figure 6:
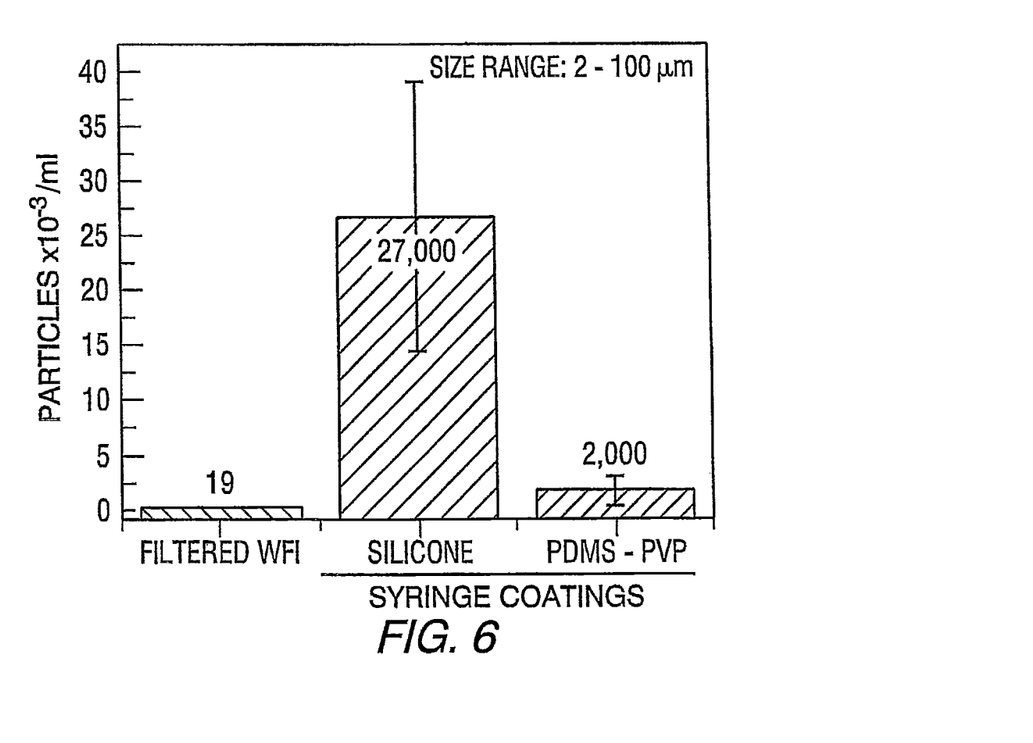
FIG. 6 is a graph of particle concentration of water for injection (WFI) after storage for 1 hour in syringes having interior barrel coatings as specified.

The concentration of particles in a solution of filtered water for injection was evaluated for a control sample in an uncoated glass syringe ("Filtered WFI"), a syringe coated with DC 360 polydimethylsiloxane only, in a manner as described above ("Silicone"), and a syringe prepared according to the present invention as described above coated with DC 360 polydimethylsiloxane and polyvinylpyrrolidone ("PDMS-PVP"). The concentration of microparticles was determined at room temperature (about 25° C.) using Micro-Flow Imaging™ particle analysis available from Brightwell Technologies Inc. FIG. 6 is a graph of particle concentration of water for injection (WFI) after storage for 1 hour in the syringes. The particle size range included in the analysis was 2-100 µm. As shown in FIG. 6, the Filtered WFI had a particle concentration of only 19 particles/ml. However, the water in the Silicone treated syringe had a particle concentration of 27,000 particles/ml. In contrast, the water in the PT Silicone treated syringe had a particle concentration of 2000 particles/ml and the water in the PDMS-PVP treated syringe had a particle concentration of 2,000 particles/ml. FIG. 6 shows that the PDMS-PVP coated sample syringe according to the present invention had a much lower concentration of particles compared to the silicone only coated syringe.

Figure 7:
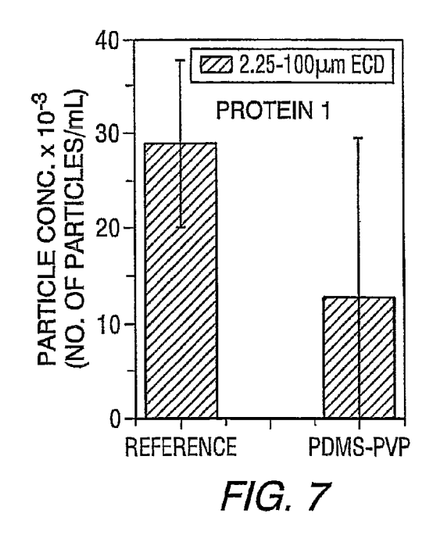
FIG. 7 is a graph of particle concentration in protein solutions stored in syringes having interior barrel coatings as specified.

FIG. 7 is a graph of particle concentration in an aqueous solution of recombinant protective antigen of anthrax (rPA) protein solution at 120 µg/ml ("Protein 1") in a Hypak™ glass syringe having an interior barrel coating of polydimethylsiloxane only ("Reference") and a sample of the same protein solution in a syringe coated with PDMS-PVP as set forth above, after storage for 6 hours. As shown in FIG. 7, the sample contained in the syringe coated with PDMS-PVP had only about 13,000 particles/ml, compared to the sample in the uncoated syringe which had about 29,000 particles/ml.

Figure 8:
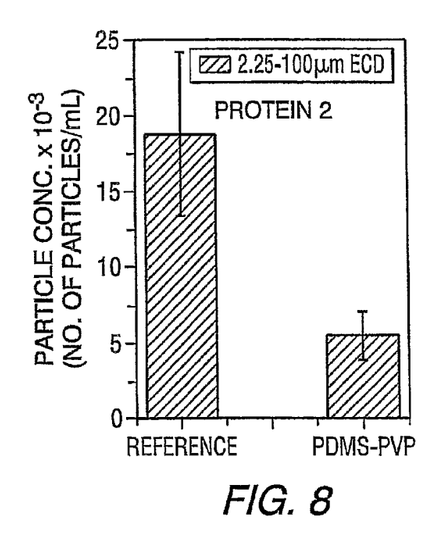
FIG. 8 is a graph of particle concentration in protein solutions stored in syringes having interior barrel coatings as specified.

FIG. 8 is a graph of particle concentration in an aqueous solution of monoclonal anti-staphylococcal enterotoxin antibody (anti-rSEB mAb) at 4 mg/ml ("Protein 2") in a glass syringe having an interior barrel coating of polydimethylsiloxane only ("Reference") and a sample of the same protein solution in a syringe coated with PDMS-PVP as set forth above, after storage for 1 hour. As shown in FIG. 8, the sample contained in the syringe coated with PDMS-PVP had only about 6,000 particles/ml, compared to the sample in the uncoated syringe which had about 18,000 particles/ml.

Figure 9:
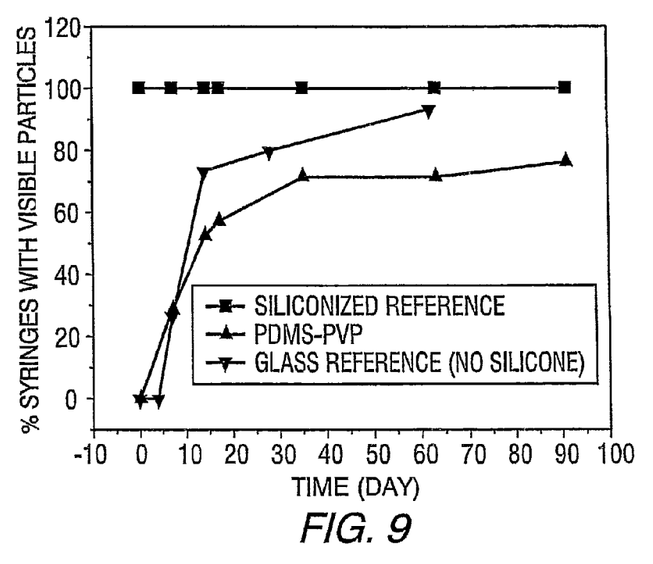
FIG. 9 is a graph of percentage of syringes with visible particles as a function of elapsed time (days)

The rate of development of visible particles in syringes having no interior coating ("Glass reference"), syringes having an interior coating of polydimethylsiloxane ("Siliconized reference"), syringes having an interior coating of PDMS-PVP as above ("PDMS-PVP") was evaluated for 21 of syringes of each type, each syringe being filled with Orencia® abatacept solution at 25 mg/ml (available from Bristol-Myers Squibb), which is known to exhibit sensitivity to silicone. FIG. 9 is a graph of percentage of syringes with visible particles as a function of elapsed time (days), which shows that the rate of development of visible particles in the solution is much lower in the PDMS-PVP coated syringes compared to the Siliconized reference syringes. The rate of development of visible particles in the solution in the PDMS-PVP coated syringes is comparable to the Glass reference, which had no silicone coating.

Breakout forces, breakloose forces, and sustaining forces may be conveniently measured on a universal mechanical tester or on a testing machine of the type having a constant rate of cross-head movement, as described in detail below. Selected syringe assemblies were evaluated for breakloose force according to ISO 7886-1 Annex G. The breakloose (actuation) and sustaining force (in kilograms) of each sample syringe was determined by an Instron Series 5500 at a displacement rate of 380 mm/min according to ISO 7886. The breakloose force is visually determined as the highest peak of the curve or point of where the slope of the curve changes on the graph. The sustaining force is the average force for the stopper to move an additional 25-30 mm for a 1 ml barrel or an additional 115-120 mm for a 20 ml barrel after breakloose. The gliding performance can be summarized by the absolute value of the force required to displace the stopper from initial position and the maximum value of the force needed to sustain its displacement. Lower values are representative of higher performance.

Figure 10:
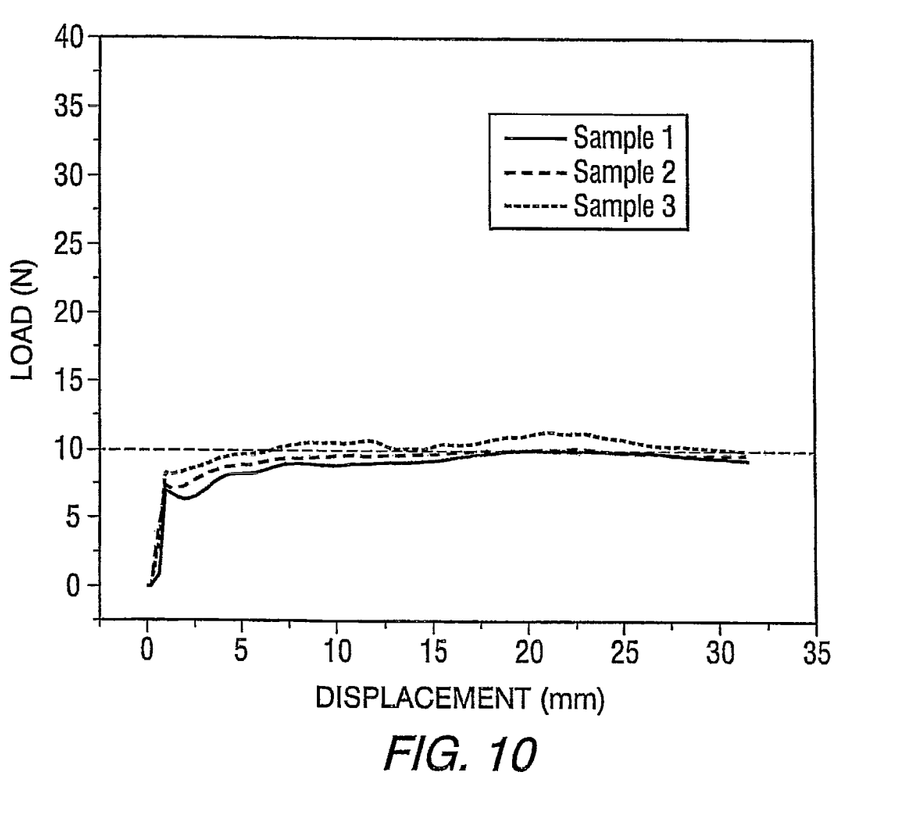
FIG. 10 is a graph of actuation and gliding force (N) as a function of displacement (mm) for three samples of a syringe having an interior barrel coatings according to the present invention.

FIG. 10 is a graph of actuation and gliding force (N) as a function of displacement (mm) between a butyl rubber stopper and a HYPAK™ 1 ml glass syringe barrel coated with PDMS-PVP as described above, according to the present invention. The three lines correspond to three replicate samples for the same coated substrate.

The present invention has been described with reference to specific details of particular embodiments thereof. It is not intended that such details be regarded as limitations upon the scope of the invention except insofar as and to the extent that they are included in the accompanying claims.

What is claimed is:

1. A medical article comprising a substrate having a coating on a surface thereof, the coating comprising: (1) at least one organopolysiloxane and (2) a deposition product applied to the at least one organopolysiloxane by plasma-enhanced chemical vapor deposition of a composition comprising at least one monomer selected from the group consisting of N-vinyl pyrrolidone, vinyl acetate, ethylene oxide, alkyl acrylate, alkyl methacrylate, acrylamide, acrylic acid, and mixtures thereof.

2. The medical article according to claim 1, wherein the medical article is selected from the group consisting of a chamber and a sealing member.

3. The medical article according to claim 2, wherein the chamber has a contact surface adapted to sealingly engage a contact surface of a sealing member for a medical article.

4. The medical article according to claim 3, wherein the coating comprises the contact surface of the chamber.

5. The medical article according to claim 1, wherein the chamber is selected from the group consisting of a syringe barrel, drug cartridge container, needleless injector container, liquid dispensing device container, liquid metering device container, sample collection tube, catheter, and vial.

6. The medical article according to claim 5, wherein the chamber is a syringe barrel.

7. The medical article according to claim 1, wherein the chamber is formed from glass, metal, ceramic, plastic, or combinations thereof.

8. The medical article according to claim 7, wherein the chamber is prepared from an olefinic polymer selected from the group consisting of polyethylene, polypropylene, poly(1-butene), poly(2-methyl-1-pentene), cyclic polyolefins, and mixtures thereof.

9. The medical article according to claim 2, wherein the sealing member has a contact surface adapted to sealingly engage a contact surface of a chamber for a medical article.

10. The medical article according to claim 9, wherein the coating comprises the contact surface of the sealing member.

11. The medical article according to claim 2, wherein the sealing member is selected from the group consisting of a stopper, O-ring, V-ring, plunger tip, and piston.

12. The medical article according to claim 2, wherein the sealing member is formed from rubber.

13. The medical article according to claim 1, wherein the organopolysiloxane is polydimethylsiloxane.

14. The medical article according to claim 1, wherein the organopolysiloxane is represented by the following structural Formula (I):

(I)

wherein each R is an independently selected alkyl group and Z is about 30 to about 4,500.

15. The medical article according to claim 1, wherein the alkyl acrylate is selected from the group consisting of methyl acrylate, ethyl acrylate, butyl acrylate, and mixtures thereof.

16. The medical article according to claim 1, wherein the alkyl methacrylate is methyl methacrylate.

17. The medical article according to claim 1, wherein the monomer is N-vinyl pyrrolidone.

18. The medical article according to claim 1, wherein the concentration of the at least one organopolysiloxane is greater near the surface of the substrate.

19. The medical article according to claim 1, wherein a portion of the at least one organopolysiloxane is adjacent to an outer surface of the coating.

20. The medical article according to claim 1, wherein a portion of the at least one monomer chemically reacts with a portion of the at least one organopolysiloxane.

21. The medical article according to claim 1, wherein the at least one organopolysiloxane is applied to the surface of the substrate; and the deposition product is applied to the at least one organopolysiloxane by plasma-enhanced chemical vapor deposition.

22. The medical article according to claim 1, wherein the deposition of the at least one monomer forms an integrated coating with the at least one organopolysiloxane.

23. A syringe barrel having a coating on an inner surface thereof, the coating comprising at least one organopolysiloxane applied to the inner surface of the syringe barrel and a deposition product applied thereon, the deposition product being prepared by plasma-enhanced chemical vapor deposition of a composition comprising at least one monomer selected from the group consisting of N-vinyl pyrrolidone, vinyl acetate, ethylene oxide, alkyl acrylate, alkyl methacrylate, acrylamide, acrylic acid, and mixtures thereof.

24. A method for coating a surface of a medical article, comprising:
    (a) applying a first coating comprising at least one organopolysiloxane to a surface of a substrate; and
    (b) applying a deposition product to at least a portion of the first coating by plasma-enhanced chemical vapor deposition of a composition comprising at least one monomer selected from the group consisting of N-vinyl pyrrolidone, vinyl acetate, ethylene oxide, alkyl acrylate, alkyl methacrylate, acrylamide, acrylic acid, and mixtures thereof.

25. A method for lubricating an interface between an inner surface of a chamber and an exterior surface of a sealing member of a medical article, comprising:
    (a) applying a first coating comprising at least one organopolysiloxane onto the interior surface of the chamber and/or the exterior surface of the sealing member;
    (b) applying a deposition product to at least a portion of the first coating by plasma-enhanced chemical vapor deposition of a composition comprising at least one monomer selected from the group consisting of N-vinyl pyrrolidone, vinyl acetate, ethylene oxide, alkyl acrylate, alkyl methacrylate, acrylamide, acrylic acid, and mixtures thereof.

26. The medical article according to claim 1, wherein a higher concentration of the deposition product of the at least one monomer is present near an outer surface of the coating compared to within a bulk of the coating.

* * * * *